United States Patent
Kim et al.

(10) Patent No.: US 9,961,754 B2
(45) Date of Patent: May 1, 2018

(54) METHOD FOR REMOVING OF RESIDUAL CHARGE, X-RAY IMAGING METHOD AND APPARATUS USING THE METHOD

(71) Applicant: Samsung Electronics Co., Ltd., Suwon-Si, Gyeonggi-Do (KR)

(72) Inventors: Young Kim, Yongin-si (KR); Sunil Kim, Osan-si (KR); Jaechul Park, Yangju-si (KR); Kangho Lee, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 308 days.

(21) Appl. No.: 14/476,069

(22) Filed: Sep. 3, 2014

(65) Prior Publication Data

US 2015/0063544 A1 Mar. 5, 2015

(30) Foreign Application Priority Data

Sep. 4, 2013 (KR) .................. 10-2013-0106307

(51) Int. Cl.
*H05G 1/30* (2006.01)
*G01N 23/04* (2018.01)
*G03G 15/22* (2006.01)
*H01L 27/146* (2006.01)
*G01T 1/24* (2006.01)

(52) U.S. Cl.
CPC .............. *H05G 1/30* (2013.01); *G01N 23/04* (2013.01); *G01T 1/24* (2013.01); *G03G 15/222* (2013.01); *H01L 27/14676* (2013.01)

(58) Field of Classification Search
CPC .................. G01N 23/04; G03G 15/222; H01L 27/14676; G01T 1/24
See application file for complete search history.

(56) References Cited

U.S. PATENT DOCUMENTS

| | | | | |
|---|---|---|---|---|
| 4,906,855 A | * | 3/1990 | Berger | H04N 3/1512 257/E27.141 |
| 5,510,626 A | * | 4/1996 | Nelson | G01T 1/246 250/580 |
| 5,563,421 A | * | 10/1996 | Lee | G01T 1/24 250/370.09 |

(Continued)

FOREIGN PATENT DOCUMENTS

| | | |
|---|---|---|
| JP | 2010131223 A | 6/2010 |
| KR | 100361470 B1 | 11/2002 |

(Continued)

OTHER PUBLICATIONS

Extended European Search Report dated Jan. 29, 2015 for corresponding Application No. EP 14183420.0-1560.

*Primary Examiner* — Christine Sung (57) ABSTRACT

A method of removing residual charge from a photoconductive material includes applying a first voltage to the photoconductive material to form an electrostatic field during a collection operation in which x-rays are irradiated onto the photoconductive material; and applying a second voltage to the photoconductor to reduce an amount of residual charge therein during a removal operation, the second voltage being different from the first voltage. In one or more example embodiments, the photoconductive material may include Mercury Iodine ($HgI_2$).

18 Claims, 9 Drawing Sheets

(56) References Cited

U.S. PATENT DOCUMENTS

| | | | | |
|---|---|---|---|---|
| 5,661,309 A | * | 8/1997 | Jeromin | G03G 15/758 |
| | | | | 250/370.09 |
| 5,880,472 A | * | 3/1999 | Polischuk | G03G 5/0433 |
| | | | | 250/370.09 |
| 5,969,360 A | * | 10/1999 | Lee | H04N 5/2175 |
| | | | | 250/370.09 |
| 6,078,053 A | * | 6/2000 | Adam | G03G 13/054 |
| | | | | 250/370.08 |
| 6,359,965 B1 | | 3/2002 | Finkler et al. | |
| 6,518,576 B2 | | 2/2003 | Kim | |
| 6,723,995 B2 | * | 4/2004 | Rougeot | G21K 4/00 |
| | | | | 250/370.11 |
| 6,803,957 B1 | | 10/2004 | MacHida et al. | |
| 6,818,898 B2 | | 11/2004 | Kim | |
| 2007/0096035 A1 | * | 5/2007 | Lmai | G01T 1/24 |
| | | | | 250/370.12 |
| 2013/0221241 A1 | * | 8/2013 | Rowlands | H01L 31/115 |
| | | | | 250/473.1 |
| 2015/0103975 A1 | * | 4/2015 | Yang | G01T 1/246 |
| | | | | 378/62 |

FOREIGN PATENT DOCUMENTS

| | | |
|---|---|---|
| KR | 100394461 B1 | 8/2003 |
| KR | 20110019158 A | 2/2011 |

* cited by examiner

METHOD FOR REMOVING OF RESIDUAL CHARGE, X-RAY IMAGING METHOD AND APPARATUS USING THE METHOD

CROSS-REFERENCE TO RELATED APPLICATIONS

This application claims the benefit of Korean Patent Application No. 10-2013-0106307, filed on Sep. 4, 2013, in the Korean Intellectual Property Office, the disclosure of which is incorporated herein in its entirety by reference.

BACKGROUND

1. Field

Example embodiments relate to methods of removing residual charges, for example, in a photoconductor layer constituting an X-ray detector and X-ray imaging methods and apparatuses using the residual charge removing method.

2. Description of the Related Art

An X-ray imaging system is widely used in various fields such as industrial, scientific, and medical fields for non-destructive testing, testing of structure and properties of materials, diagnostic imaging, and to assist in performing security checks. Generally, an X-ray imaging system includes an X-ray emitter which emits an X-ray and an X-ray detector which detects an X-ray transmitted through a target object.

An X-ray emitter generally emits X-rays by colliding electrons emitted from an electron-emitting device (e.g. a cathode) to an anode. Electron-emitting devices may include hot cathode devices and cold cathode devices. A hot cathode an electrode that is heated by electric current passing through a filament while a cold cathode is an electrode that is not electrically heated by a filament but instead may rely on field emissions (FE).

In the absence of a strong electric field, electrons may need to acquire a certain minimum energy, called a work function to be emitted. In contrast, in field emission (FE) techniques, the emission of electrons may be induced by an electrostatic field. An electron emitting device utilizing field emission may be driven at a relatively low voltage. Therefore, there is research in progress for commercialization of electron-emitting devices utilizing field emission.

An x-ray system may be analog or digital. In a digital x-ray system, an image may be generated by indirectly converting photons from the x-ray into an electrical signal via visible light or directly converting the x-ray photons into the electrical signal using a photoconductor. By directly converting the x-rays into electric signals, the imaging device may generate an image with a relatively high resolution.

In digital x-rays systems, there may be residual photons held in the photoconductor within a frame which may cause a phenomenon known as an after image in which artifacts from previous X-ray exposures are visible in later X-ray images. Such undesirable image artifacts decay in a lag time which may be a limitation in high-speed x-ray machines.

Conventionally, after-images may be removed by uniformly irradiating the photoconductor with visible light to generate new charges to combine with the residual charges or applying a reverse bias voltage to the photoconductor to force the charges to recombine. However, irradiating visible light onto the photoconductor, alone, may require a relatively long period of exposure time (e.g. several dozen seconds) to effectively remove the residual charges. Further, conventional photoconductor materials have a relatively high bias voltage. For example, amorphous selenium (a-Se) may require a bias voltage of several kilovolts (kV). Therefore, applying a reverse bias voltage to a conventional photoconductor may require a relatively high bias voltage. To generate such a high bias voltage, a detector may need to include a high voltage generator which may take up a relative large portion of the detector, thus increasing the size thereof. Further, when a material having a high bias voltage is used, switching between a bias voltage and a sufficient voltage having an opposite polarity to recombine the residual charges may take a relatively long time and put unnecessary strain on the electrical components of the detector, which may cause reliability issues.

SUMMARY

Provided are methods for removing residual charges in a photoconductor layer, x-ray imaging methods and an x-ray detector employing the same.

Additional aspects will be set forth in part in the description which follows and, in part, will be apparent from the description, or may be learned by practice of the example embodiments.

One or more example embodiments relates to a method of removing residual charges from a photoconductive material.

In some example embodiments, the method includes applying a first voltage to the photoconductive material to form an electrostatic field during a collection operation in which x-rays are irradiated onto the photoconductive material; and applying a second voltage to the photoconductor to reduce an amount of residual charge therein during a removal operation, the second voltage being different from the first voltage.

In some example embodiments, the first voltage has a magnitude of less than 300 volts (V) and the photoconductive material is a material configured to operate at the first voltage.

In some example embodiments, the photoconductive material includes Mercury Iodine ($HgI_2$).

In some example embodiments, the method further includes determining a reference voltage based on the amount of residual charge; and determining the second voltage based on the reference voltage.

In some example embodiments, the applying a second voltage includes applying a second voltage that has a polarity opposite that of the first voltage and an absolute value smaller than that of the first voltage.

In some example embodiments, the applying a second voltage includes applying a second voltage that has a same polarity as the first voltage and an absolute value greater than that of the first voltage.

In some example embodiments, the reducing an amount of residual charge by applying a second voltage includes applying the second voltage to the photoconductive material in a form of a plurality of pulses.

In some example embodiments, the method further includes applying visible light to the photoconductive material during the removal operation.

In some example embodiments, the applying visible light to the photoconductive material includes applying the visible light to the photoconductor simultaneously with the second voltage.

In some example embodiments, the method further includes storing at least a portion of charges generated in the photoconductive material during the collection operation; and reading out the stored charges to form a first frame image before the removal operation.

One or more example embodiments relates to a method of forming an x-ray image.

In some example embodiments, the method includes irradiating a target object with x-rays during a collection operation, at least a portion of the irradiated x-rays being transmitted through the target object onto a photoconductive material; applying a first voltage to the photoconductive material to form an electrostatic field during the collection operation; and applying a second voltage to the photoconductor to reduce an amount of residual charge therein during a removal operation, the second voltage being different from the first voltage.

In some example embodiments, the photoconductive material includes Mercury Iodine (HgI$_2$), and the first voltage has a magnitude of less than 300 volts (V).

In some example embodiments, the method further includes storing at least a portion of charges generated in the photoconductive material during the collection operation; and reading out the stored charges to form a first frame image before the removal operation.

In some example embodiments, a second x-ray image may be formed after the removal operation such that residual charges from the first frame image are not present in the photoconductive material during the forming of the second x-ray image.

One or more example embodiments relates to an x-ray detector.

In some example embodiments, the x-ray detector includes a photoconductor and a control unit. The control unit may be configured to, apply a first voltage to the photoconductor to form an electrostatic field during a collection operation in which x-rays are irradiated onto the photoconductor, and apply a second voltage to the photoconductor to reduce an amount of residual charge therein during a removal operation, the second voltage being different from the first voltage.

In some example embodiments, the photoconductor includes Mercury Iodine (HgI$_2$).

In some example embodiments, the first voltage has a magnitude of less than 300 volts (V).

In some example embodiments, the x-ray detector further includes a common electrode on a first surface of the photoconductor, the common electrode; at least one pixel electrode on a second surface of the photoconductor; and a bias voltage source connected between the common electrode and the at least one pixel electrode, the bias voltage source configured to generate the first voltage and the second voltage based on a control signal from the control unit.

In some example embodiments, the x-ray detector further includes a charging capacitor configured to store charges received from the pixel electrodes; and a switch configured to provide the stored charges to a read-out circuit based on a gate voltage applied to the switch.

In some example embodiments, the control unit is configured to instruct the bias voltage source to generate the second voltage such that the second voltage has a polarity opposite that of the first voltage and an absolute value smaller than that of the first voltage.

In some example embodiments, the control unit is configured to instruct the bias voltage source to generate the second voltage such that the second voltage has a same polarity as the first voltage and an absolute value greater than that of the first voltage.

In some example embodiments, the control unit is configured to instruct the bias voltage source to generate the second voltage such that the second voltage is applied to the photoconductor as a plurality of pulses.

In some example embodiments, the control unit is configured to apply visible light to the photoconductor during the removal operation.

In some example embodiments, the control unit is configured to, determine a reference voltage based on the amount of residual charge, and determine the second voltage based on the reference voltage.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Example embodiments will now be described more fully with reference to the accompanying drawings, in which some example embodiments are shown. In the drawings, the thicknesses of layers and regions are exaggerated for clarity. Like reference numerals in the drawings denote like elements.

Detailed illustrative example embodiments are disclosed herein. However, specific structural and functional details disclosed herein are merely representative for purposes of describing example embodiments. Example embodiments may be embodied in many alternate forms and should not be construed as limited to only those set forth herein.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of this disclosure. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

The example embodiments may be described in terms of functional block components and various processing steps. Such functional blocks may be realized by any number of hardware and/or software components configured to perform the specified functions.

The term 'X-ray image' may refer to an image regarding a target object obtained by using an X-ray. The target object may include a human, an animal, or a portion of a human or an animal. The target object may include organs and/or blood vessels of the human or animal. For example, the target object may include a liver, a heart, a uterus, a brain, a breast, and/or an abdomen.

Various example embodiments will now be described more fully with reference to the accompanying drawings in which some example embodiments are shown. In the drawings, the thicknesses of layers and regions are exaggerated for clarity.

Figure 1:
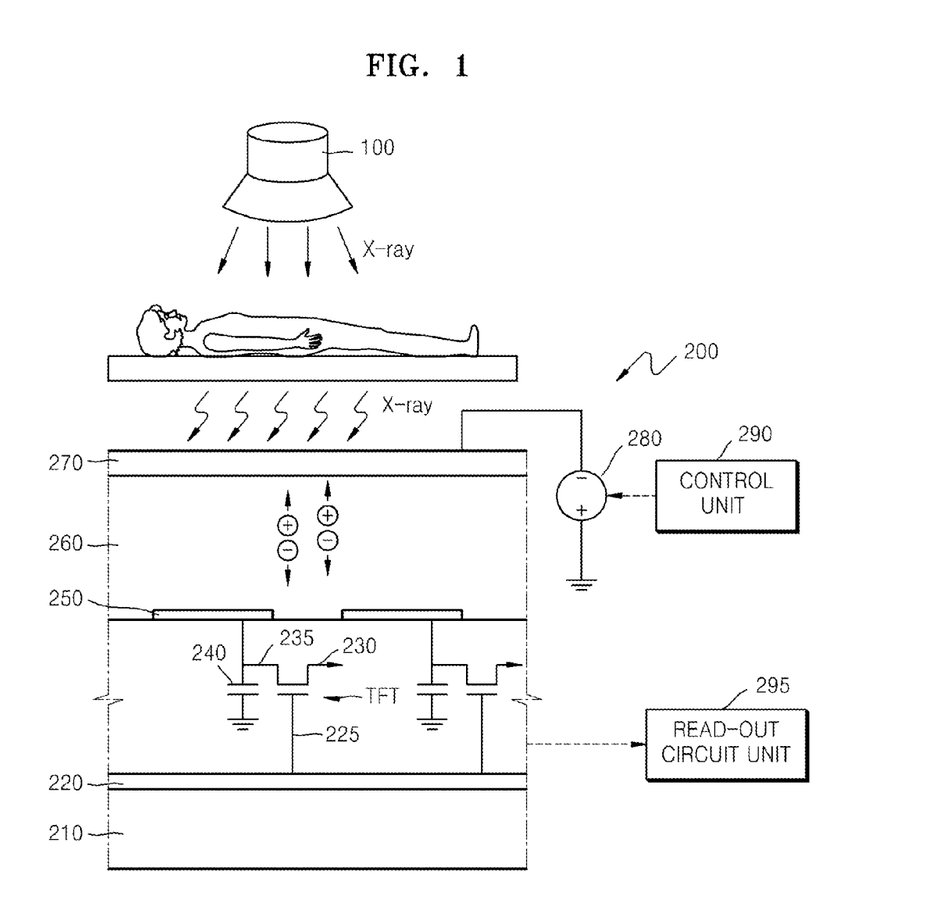
FIG. 1 is a diagram showing an example structure of an X-ray detector for describing a method of removing residual charges according to an example embodiment.
Figure 2:
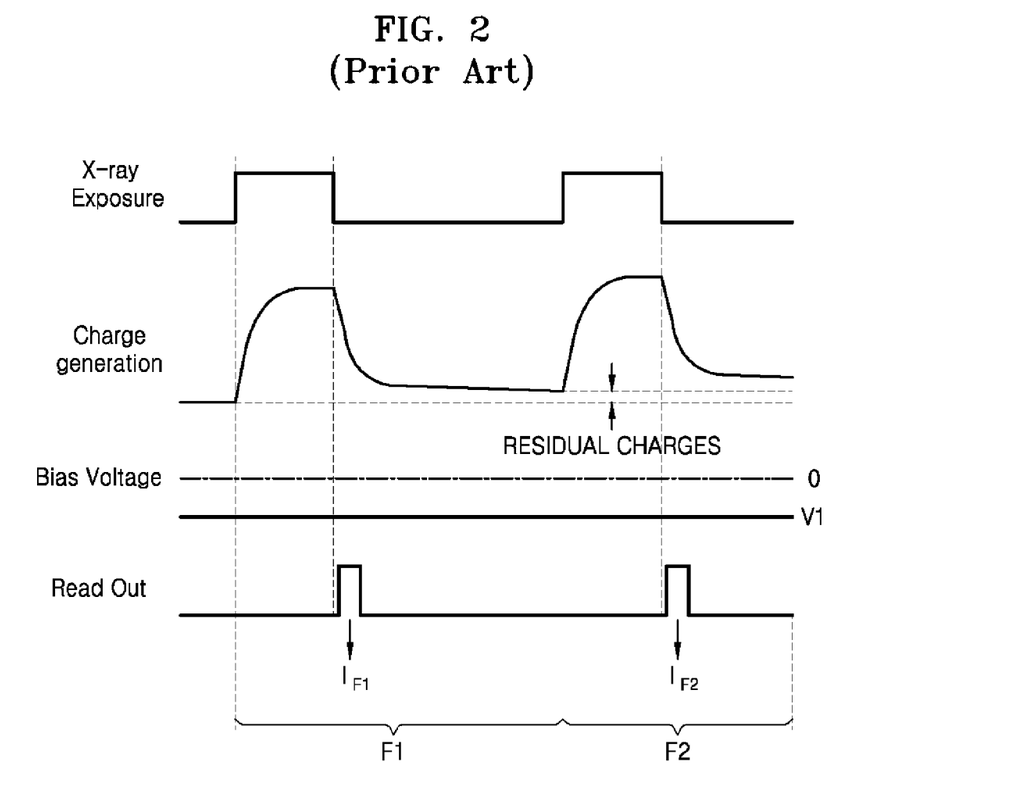
FIG. 2 is a graph illustrating residual charges remaining between frame images in a conventional X-ray detector using a fixed bias voltage.
Figure 3:
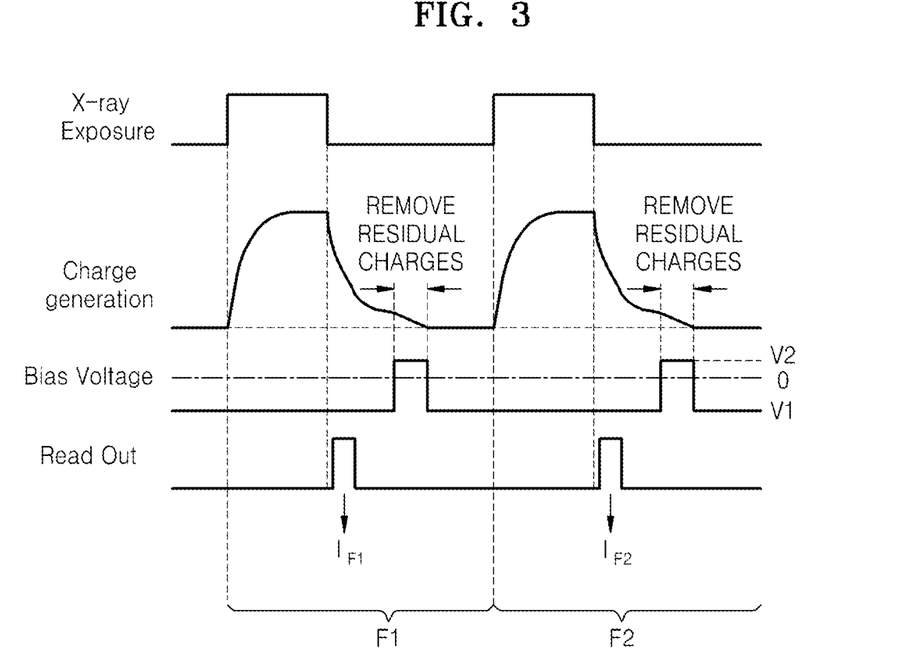
FIG. 3 is a graph illustrating the removal of residual charges between frame images using an X-ray detector having a variable bias voltage according to some example embodiments.

FIG. 1 is a diagram showing an example structure of an X-ray detector configured to remove residual charges according to an example embodiment, and FIGS. 2 through 4 are graphs showing relationships between X-ray irradiation, charges formed thereby and reading signals.

Referring to FIG. 1, in an X-ray imaging device, an X-ray detector 200 is configured to detect an X-ray, which is emitted by an X-ray emitter 100 and transmitted through a target object, and output corresponding electric signals.

The X-ray detector 200 may include a photoconductor layer 260 which detects the X-ray, a top electrode 270 to which a voltage is applied for forming an electric field at the photoconductor layer 260 to utilize a field emission (FE) technique, and a pixel electrode 250 for collecting charges formed in the photoconductor layer 260.

The X-ray detector 200 may further include a charging capacitor 240 in which charges collected by the pixel electrode 250 are stored connected to a drain 235 of a thin-film transistor TFT. The TFT may be configured to selectively provide the charges stored in the charging capacitor 240 to a data line (not shown) connected to a source 230 of the TFT based on a voltage applied to a gate 225 of the TFT. The TFT may be formed on a substrate 210 on which a gate line 220 is formed. The gate line 220 may be connected to the gate 225 of the TFT.

The photoconductor layer 260 may be formed of one or more photoconductor materials which react with an X-ray and generates charges. In one or more example embodiments the photoconductor layer 260 may be formed of Mercury Iodine $HgI_2$. However, the photoconductor layer 260 may be formed of other materials which are sensitive to x-rays and have a relatively low bias voltage. For example, the photoconductor layer 260 may be formed of $PbI_2$, CdTe, CdZnTe, PbO, or $PbO_2$.

The x-ray detector 200 may include an insulation layer, if necessary (not shown). For example, the insulation layer may be included based on a material constituting the photoconductor layer 260. The insulation layer may be between the photoconductor layer 260 and the top electrode 270 or between the photoconductor layer 260 and the pixel electrode 250.

The insulation layer may be configured to block off current by preventing electrons and holes from moving and being leaked before an electric field is formed in the photoconductor layer 260 by a bias voltage source 280.

The bias voltage source 280 may apply a voltage to the top electrode 270 to form an electric field at the photoconductor layer 260. The voltage applied to the top electrode 270 may be based on the materials constituting the photoconductor layer 260. For example, in a conventional X-ray detector having a photoconductor layer 260 formed of amorphous selenium (a-Se), a voltage of several kilovolts kV may be necessary to generate a sufficient electric field.

In contrast, in one or more example embodiments, the photoconductor layer 260 is formed of Mercury Iodine $HgI_2$, therefore, a relatively low voltage (e.g. −20V~−200V to +300V) may generate a sufficient electric field.

The photo detector 200 may further include a control unit 290 and a read-out circuit unit 295. The control unit 290 may control the bias voltage source 280 to adjust the voltage applied to the top electrode 270. For example, the control unit 290 may instruct the bias voltage source 280 to apply one of a first voltage and a second voltage, which is different from the first voltage, to the top electrode 270.

A single bias voltage source 280 may be used to apply the first voltage V1 and the second voltage V2 to the top electrode 270 such that the bias voltage source 280 may toggle applied voltages. The toggling operation may be relatively less strenuous on the voltage source 280 when the voltage applied to the photoconductor layer 260 has a small value, for example, when the photoconductor layer 260 is formed of Mercury Iodine $HgI_2$ having a low driving voltage, for example.

When the bias voltage source 280 applies the first voltage to the top electrode 270 under the control of the control unit 290, the X-ray detector 200 may operate in a collection mode to collect charges formed in the photoconductor layer 260 due to the X-ray irradiation. As discussed in more detail below with reference to FIG. 3, when the bias voltage source 280 applies the second voltage, which is different from the first voltage, to the top electrode 270, the X-ray detector 200 may operate in a removal mode to remove residual charges remaining in the photoconductor layer 260 after the X-ray irradiation.

When the X-ray is irradiated through the target object onto the photoconductor layer 260. The X-ray incident to the photoconductor layer 260 generates electron-hole pairs in the photoconductor layer 260. When a voltage is applied by the bias voltage source 280 to the top electrode 270 and an electric field is formed at the photoconductor layer 260 due to the application of the voltage, the electron-hole pairs are separated by the electric field. For example, when a negative voltage is applied to the top electrode 270, holes move toward the top electrode 270 and electrons are stored at the charging capacitor 240 via the pixel electrode 250.

The TFT functions as a switch controlling the transfer of charges stored in the charging capacitor 240 to outside via the data line connected to the source electrode 230 of the TFT. When a gate voltage is applied to the gate electrode 225 of the TFT via the gate line 220, a channel is formed between the source electrode 230 and the drain electrode 235 of the TFT. When the channel is formed, charges stored in the charging capacitor 240 are supplied to the source electrode 230 via the drain electrode 235. The charges supplied to the source electrode 230 are output via the data line connected to the source electrode 230. The date line may be connected to the readout circuit unit 295 and the readout circuit unit 295 may read the charges output thereto.

The read-out circuit unit may include an analog-to-digital converter (ADC) that sequentially receives data signals from the data line regarding intensities of the irradiated X-rays generates a digital signal therefrom. The output unit may further include a differential amplification unit (not shown) that removes noise from the data signals received via the data line by differentially amplifying the data signals and a reference signal. The ADC may convert the data signals from which noises are removed into digital signals suitable for displaying an image, and display the digital signals as an image on a display unit (not shown).

As described above, when an X-ray is irradiated to the photoconductor layer 260, electron-hole pairs are formed at the photoconductor layer 260, and the electron-hole pairs (e.g. charges) are separated as an electric field is created by applying a voltage to the top electrode 270. After reading out the charges for the frame, some residual charges may remain in the photoconductor layer 260. These residual charges may affect an amount of charges or electric signals thereof when an X-ray is irradiated to a target object for forming a next frame image and, thus, may cause problems like image distortions or afterimages, for example.

In one or more example embodiments, during the removal mode, the bias voltage source 280 adjusts a voltage to be applied to the top electrode 270 to remove the residual charges.

FIG. 2 is a graph illustrating residual charges remaining between frame images in a conventional X-ray detector using a fixed bias voltage.

Referring to FIG. 2, to obtain a plurality of frames of images associated with a target object, X-rays may be irradiated at a desired (or alternatively, a designated) time interval. At a first frame F1, charges formed at a photoconductor layer due to an X-ray irradiation may be collected at a pixel electrode 250 due to a bias voltage applied to a top electrode and stored at a charging capacitor via a pixel electrode 250. The electric signals may be read out and converted to a first frame image $I_{F1}$.

In the conventional x-ray detector, after the first frame F1, residual charges may remain in the photoconductor layer 260 even after X-ray irradiation for the first frame F1 is completed, and these residual charges may affect the electrical signal read during a second frame F2. Therefore, during the second frame F2, when the read-out electrical signals are converted into a second frame image IF2, the second frame image IF2 may include an afterimage due to the residual charges.

FIG. 3 is a graph illustrating the removal of residual charges between frame images using an X-ray detector having a variable bias voltage according to some example embodiments.

Referring to FIG. 3, at a first frame F1, a first voltage V1 may be applied to the top electrode 270 to read out signals for forming the first frame image IF1 and a second voltage V2 may be applied to the top electrode 270 to remove residual charges.

More specifically, the control unit 290 instructs the bias voltage source 280 to apply the first voltage V1 to the top electrode 270 when the X-ray detector 200 operates in the collection mode to collect charges formed at the photoconductor layer 260. After the charge collection and read-out of signals thereof are completed, the control unit 290 instructs the bias voltage source 280 to apply the second voltage V2 to the top electrode 270 when the X-ray detector 200 operates in the removal mode to remove residual charges remaining in the photoconductor layer 260.

The second voltage V2 is a voltage for removing residual charges remaining in the photoconductor layer 260. Polarity of the second voltage V2 may be opposite to that of the first voltage V1 and an absolute value of the second voltage V2 may be smaller than that of the first voltage V1. For example, the control unit 290 may determine an amount of residual charges remaining in a previous frame and use the amount residual charges from the previous frame as a reference for determining the second voltage V2. However, example embodiments are not limited thereto, and the magnitude and polarity of the second voltage V2 may be any voltage sufficient to remove the residual charges.

Further, in addition to applying the second voltage V2, during the removal mode, in some example embodiments, the control unit 290 may also apply visible light to the photoconductor layer 260. For example, the control unit 290 may apply a uniform pattern of light to the photoconductor layer 260 to aid in the removal of residual charges. The visible light may be applied either before the second voltage, concurrently with the second voltage or after applying the second voltage to the top electrode 270. By applying visible light along with the second voltage, the magnitude of the second voltage may be further reduced as compared to a conventional detector. The visible light may have a spectral emission and luminance sufficient to erase the afterimage.

FIGS. 4A to 4D illustrate the movement of electrons and holes in the collection and removal modes according to example embodiments.

Figure 4A:
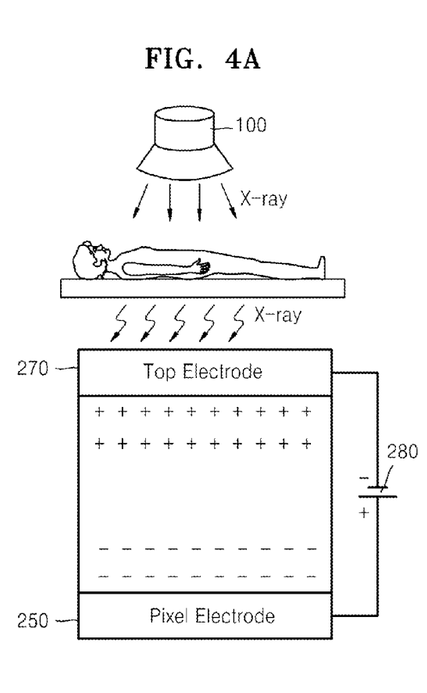
FIGS. 4A to 4D illustrate the movement of electrons and holes in the collection and removal modes according to example embodiments.

Referring to FIG. 4A, when the first voltage V1 is applied to the top electrode 270 during the collection mode, positive charges (e.g. holes) may collect at the upper portion of the photoconductor layer 260, whereas negative charges (e.g. electrons) may collect at the lower portion of the photoconductor layer 260.

Figure 4B:
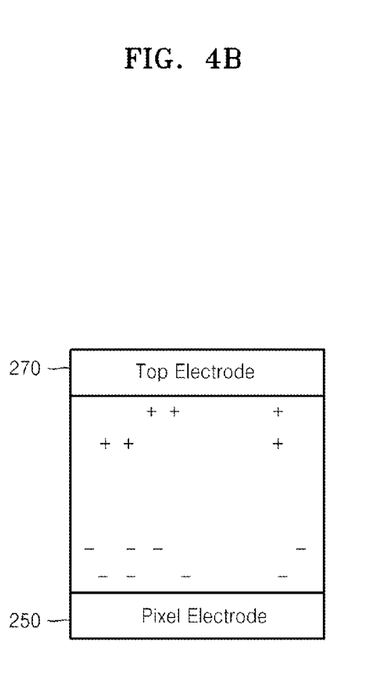

As illustrated in FIG. 4B, residual charges may remain in the photoconductor layer 260 even after X-ray irradiation for the corresponding frame is completed, and these residual charges may affect the electrical signal read during a subsequent frame.

Figure 4C:
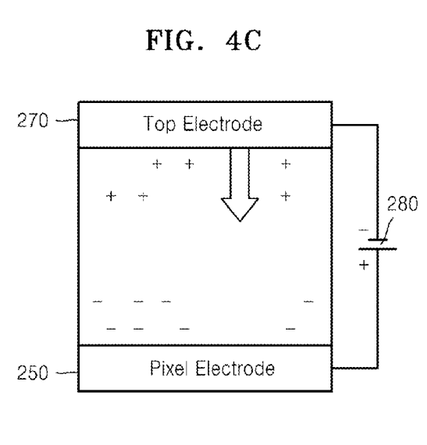

Referring to FIG. 4C, when the second voltage V2 of the opposite polarity is applied to the top electrode 270 during the removal mode, the holes in the upper portion of the photoconductor layer 260 move toward the lower portion of the photoconductor layer 260, whereas the electrons in the lower portion of the photoconductor layer 260 move toward the upper portion of the photoconductor layer 260.

Figure 4D:
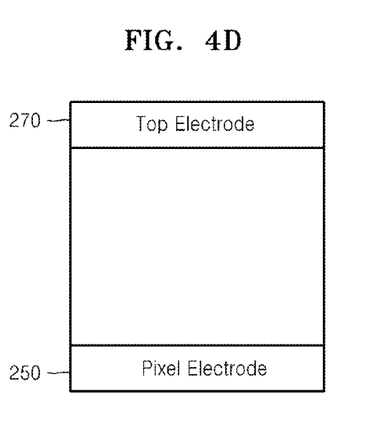

As illustrated in FIG. 4D, as a result of the movement caused by the second voltage V2, the holes and the electrons recombine with each other, thereby removing residual charges.

Next, when an X-ray is irradiated at the second frame F2 to form the second frame image IF2, charges formed at this time may not include residual charges from a previous frame. Therefore, the second frame image IF2 generated based on read-out signals associated with the second frame F2 may be a high-quality image without an afterimage or an image distortion.

Figure 5:
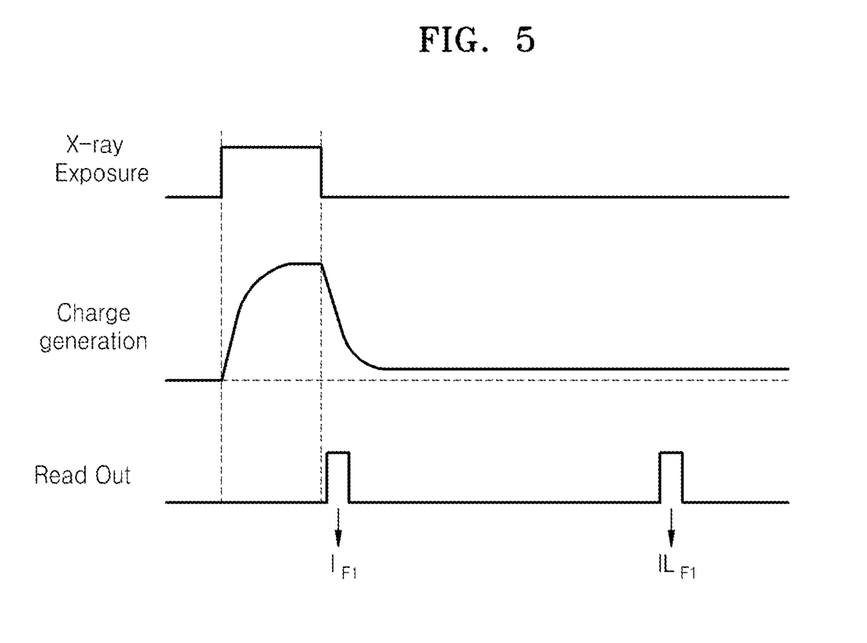
FIG. 5 is a graph showing a method of measuring residual charges to generate a reference signal according to an example embodiment.

FIG. 5 is a graph showing a method of measuring a reference signal to generate a reference signal according to an example embodiment.

Referring to FIG. 5, after an X-ray irradiation and read-out of signals for forming the first frame image IF1, a reference signal may be read out while no X-ray is irradiated. The read out reference signal may indicate an amount of the residual charges, and an image therefrom becomes a first frame lag image $IL_{F1}$. The read-out reference signals may become a reference, for example, for evaluating read-out signals and images regarding a next frame and also for determining the second voltage V2 applied for removing residual charges.

The control unit 290 may form a reference signal for each frame, or alternatively, the control unit 290 may use a same reference signal for each frame.

Figure 6:
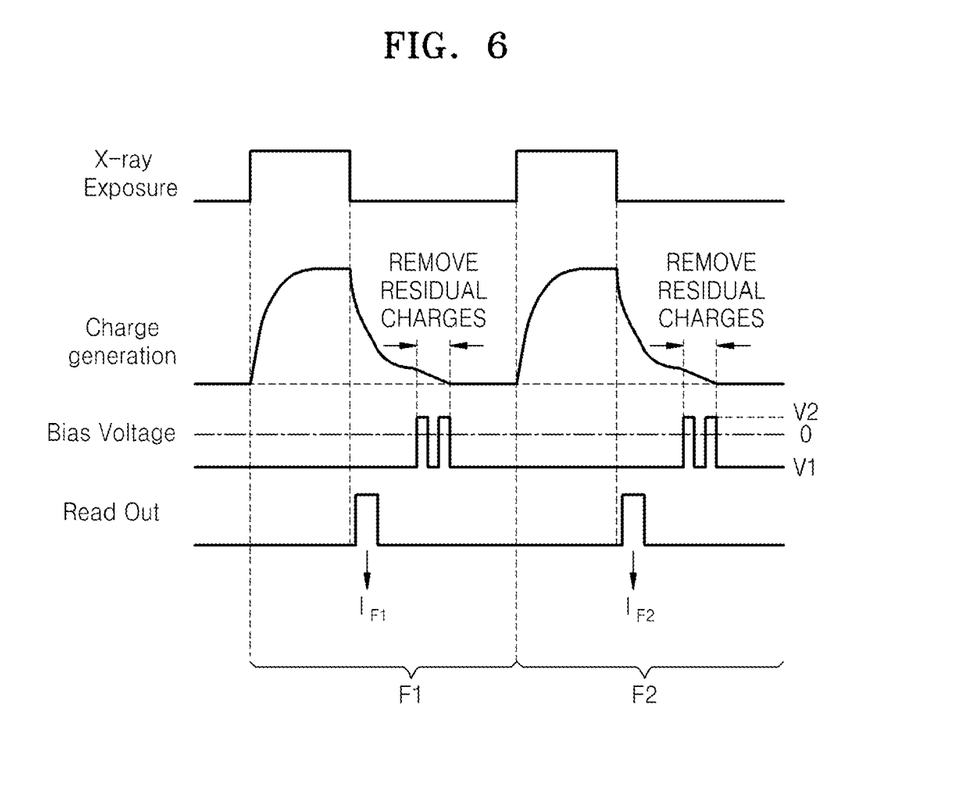
FIG. 6 is graph illustrating the removal of residual charges between frame images using an X-ray detector having a variable bias voltage according to some example embodiments.

FIG. 6 is a graph illustrating the removal of residual charges between frame images using an X-ray detector having a variable bias voltage according to some example embodiments.

As shown in FIG. 6, the second voltage V2 may be applied in the form of one or more pulses. Although the second voltage V2 is shown as two pulses in FIG. 6, example embodiments are not limited thereto. For example, the time and number of pulses may vary to effectively remove residual charges.

Figure 7:
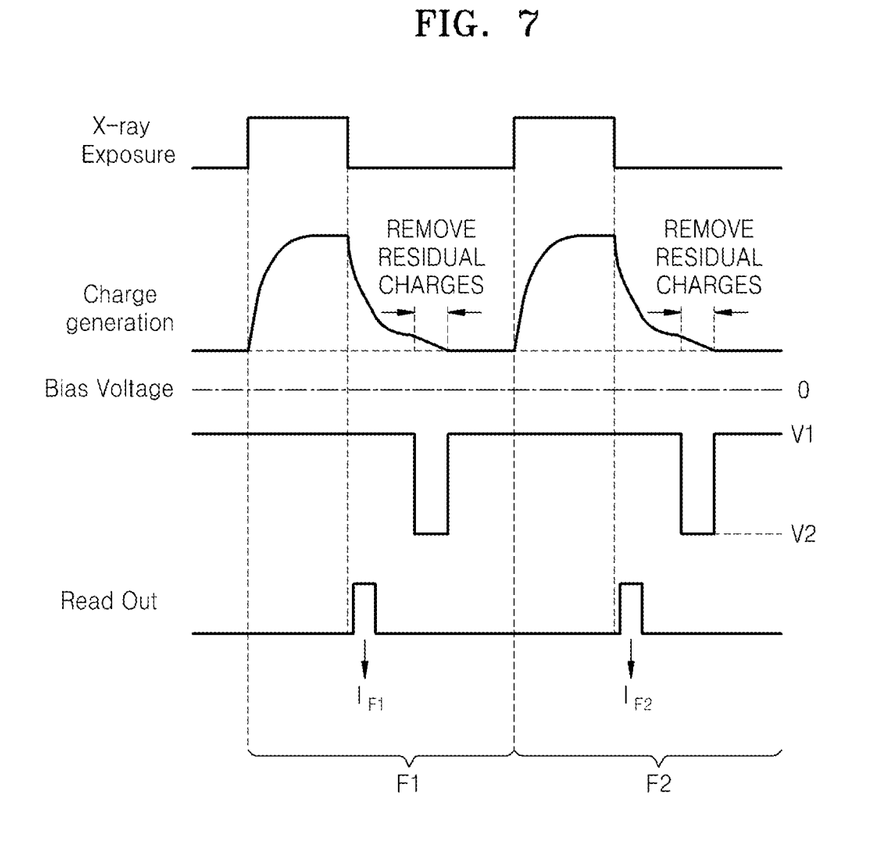
FIG. 7 is a graph illustrating the removal of residual charges between frame images using an X-ray detector having a variable bias voltage according to some example embodiments.

FIG. 7 is a graph illustrating the removal of residual charges between frame images using an X-ray detector having a variable bias voltage according to some example embodiments.

As shown in FIG. 7, a polarity of the second voltage V2 is the same as the first voltage V1 and an absolute value of the magnitude of the second voltage V2 may be greater than that of the first voltage V1. When the second voltage V2 has the same polarity as the first voltage V1, the second voltage V2 may be used to withdraw charges out of the photoconductor layer 260 by promoting movement of charges instead of inducing recombination of electrons and holes in the photoconductor layer 260. The magnitude of the second voltage V2 may be appropriately determined for the effect, and, as shown in FIG. 7, the second voltage V2 may be applied in the form of a plurality of pulses.

Although FIG. 7 illustrates a scenario where the first voltage V1 applied by the bias voltage source 280 to the top electrode 270 for collecting charges formed at the photoconductor layer 260 due to an X-ray irradiation is a negative voltage, example embodiments are not limited thereto. For example, a positive voltage may be applied to the top electrode 270 such that the electrons move to the upper portion of the photoconductor layer 260 and the holes move to the lower portion of the photoconductor layer 260. The magnitudes and polarities of the second voltage V2 as shown in FIGS. 3, 6, and 7 may be changed in correspondence thereto.

Figure 8:
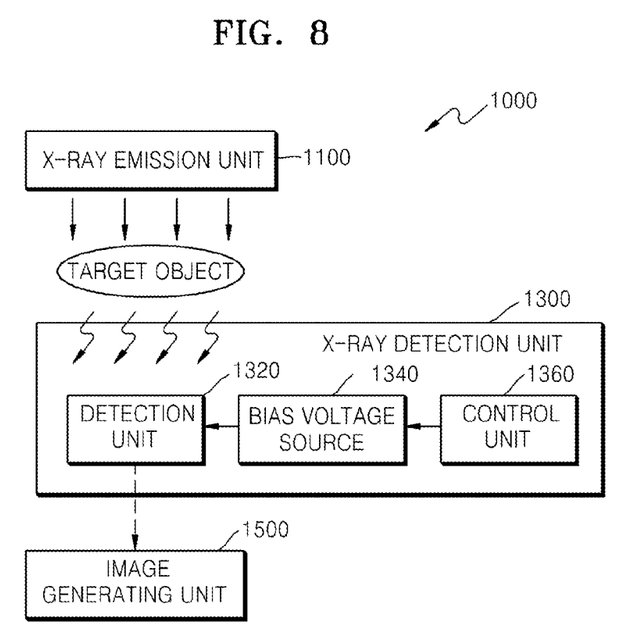
FIG. 8 is a schematic block diagram showing a X-ray imaging device according to an example embodiment.

FIG. 8 is a schematic block diagram showing an X-ray imaging device according to an example embodiment.

Referring to FIG. 8, an X-ray imaging device 1000 is configured to detect an X-ray transmitted through a target object, generate electric signals corresponding to the X-ray, and form a corresponding image based on the electric signals.

The X-ray imaging device 1000 may include an X-ray emission unit 1100 which irradiates an X-ray to a target object, an X-ray detection unit 1300 which converts an X-ray transmitted through the target object into electric signals, and an image generating unit 1500 which generates an X-ray image of the target object based on the electric signals output by the X-ray detection unit 1300.

The X-ray emission unit 1100 generally has a structure for emitting an X-ray by colliding electrons emitted by a cathode to an anode. The X-ray emission unit 1100 may employ an electron generating device using a cold cathode method, a hot cathode method, or a field emission method. The X-ray emission unit 1100 may employ various X-ray emitters and, the X-ray emission unit 1100 is not limited to the tubular type as shown in FIG. 1. For example, the X-ray emission unit 1100 may have a flat-panel-like structure. Furthermore, the X-ray emission unit 1100 may include a plurality of electron emitting units corresponding to a plurality of cells constituting a detection unit 1320 of the X-ray detection unit 1300, respectively.

The detection unit 1320 may include an X-ray detector (not shown), a bias voltage source 1340 which applies a voltage to the detection unit 1320, and a control unit 1360 which controls magnitude and polarity of the voltage formed at the bias voltage source 1340. The X-ray detector included in the detection unit 1320 may include the top electrode 270, the photoconductor layer 260, the pixel electrode 250, the TFT, and the charging capacitor 240 as shown in FIG. 1. Likewise, the bias voltage source 1340 may be embodied as the bias voltage source 280 and the control unit 1360 may be embodied as the control unit 290 illustrated in FIG. 1.

Furthermore, to form a precise image by dividing a target object into regions, a plurality of such cells may be arranged in the form of a 2D matrix. X-ray absorption of a target object varies according to type and density of a target object region through which an X-ray is transmitted or energy band of an X-ray. For example, bones may absorb more X-rays. Therefore, charges of different amounts are stored at charging capacitors of respective cells based on regions of a target object through with X-rays generated by the X-ray emission unit 1100 are transmitted, and thus the respective cells output different electric signals.

The bias voltage source 1340 is controlled by the control unit 1360 and applies a first voltage or a second voltage to the detection unit 1320. For example, the first voltage may cause the detection unit 1320 to operate in a charge collection mode, and the second voltage may cause the detection unit 1320 to operate in a residual charges removal mode. As described above with reference to FIGS. 3, 6, and 7, the polarity of the second voltage may be opposite that of the first voltage and an absolute value of the second voltage may be smaller than that of the first voltage. Alternatively, the polarity of the second voltage may be the same as that of the first voltage and the absolute value of the second voltage may be greater than that of the first voltage. The second voltage may be applied in the form of one or more pulses, and a time and a number of pulses may be based on an amount thereof that effectively removes residual charges.

The image generating unit 1500 generates an X-ray image of the target object based on electric signals output by the X-ray detection unit 1300.

The image generating unit 1500 may include a read-out circuit unit (not shown) which reads out electric signals from the X-ray detection unit 1300, an output unit (not shown) which converts signals from the read-out circuit unit into digital signals suitable for displaying an image, and a display unit (not shown) which displays an image. The read-out circuit unit may be embodied as the read-out circuit unit 295 illustrated in FIG. 1. Charges generated by a plurality of cells included in the detection unit 1320 of the X-ray detection unit 1300 are stored at respective charging capacitors.

Formation of an X-ray image from the stored charges will be briefly described below with reference to FIG. 1.

When a gate control signal is applied to the gate electrode 225 of the TFT via the gate line 220, a conductive channel is formed between the drain electrode 235 and the source electrode 230 of the TFT. Therefore, charges stored in the charging capacitors 240 of the respective cells are transmitted to the read-out circuit unit via the source electrode 230. The read-out circuit unit generates electric data signals corresponding to the charges supplied from the respective cells. Furthermore, the read-out circuit unit 295 sequentially supplies a plurality of data signals including information regarding intensities of X-rays irradiated to the respective cells and a reference signal to the analog to digital converter (ADC) (not shown) in response to an input control signal.

The read out circuit 295 may include the differential amplification unit and the analog/digital converting unit. The read out circuit 295 may include the differential amplification unit and the analog/digital converting unit. The read out circuit 295 may remove noises by differentially amplifying the data signals and the reference signal, convert the data signals from which noises are removed into digital signals suitable for displaying an image, and display the digital signals as an image on the display unit (not shown).

Figure 9:
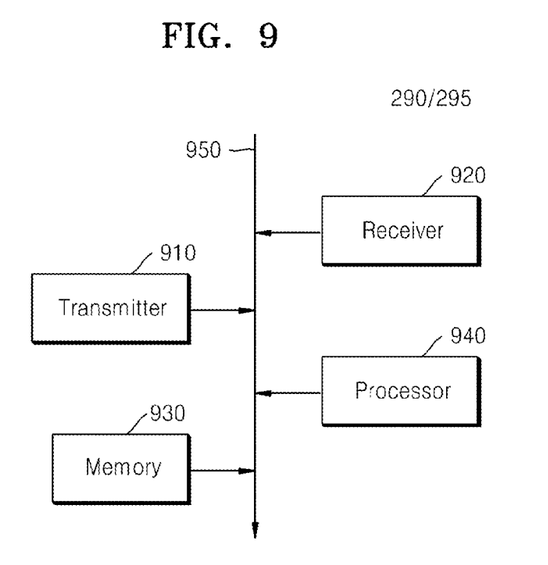
FIG. 9 illustrates a control unit and a read-out circuit unit according to example embodiments.

FIG. 9 illustrates a control unit and a read-out circuit unit according to example embodiments.

Referring to FIGS. 1 and 9, a control unit 290 and a detection unit 295 may include for example, a transmitter 910, a receiver 920, a memory 930, a processor 940, and a data bus 950.

The transmitter 910, receiver 920, memory 930, and processor 940 send data to and/or receive data from one another using the data bus 950.

The transmitter 910 may be any device having hardware and any necessary software for transmitting signals including, for example, data signals and control signals.

The receiver 920 may be any device having hardware and any necessary software for receiving signals including, for example, data signals and control signals.

The memory 930 may be any device capable of storing data including magnetic storage, flash storage, etc. The memory 930 may store, for example, information regarding the reference signal.

The processor 940 may be any device capable of processing data including, for example, a microprocessor configured to carry out specific operations by performing arithmetical, logical, and input/output operations based on input data, or capable of executing instructions included in computer readable code. The processor 940 may be a logic chip, for example, a central processing unit (CPU), a controller, or an application-specific integrated circuit (ASIC), that when, executing the instructions stored in the memory 830, configures the processor 940 as a special purpose machine. For example, the instructions may configure the processor 940 to perform the method illustrated in FIG. 10.

Figure 10:
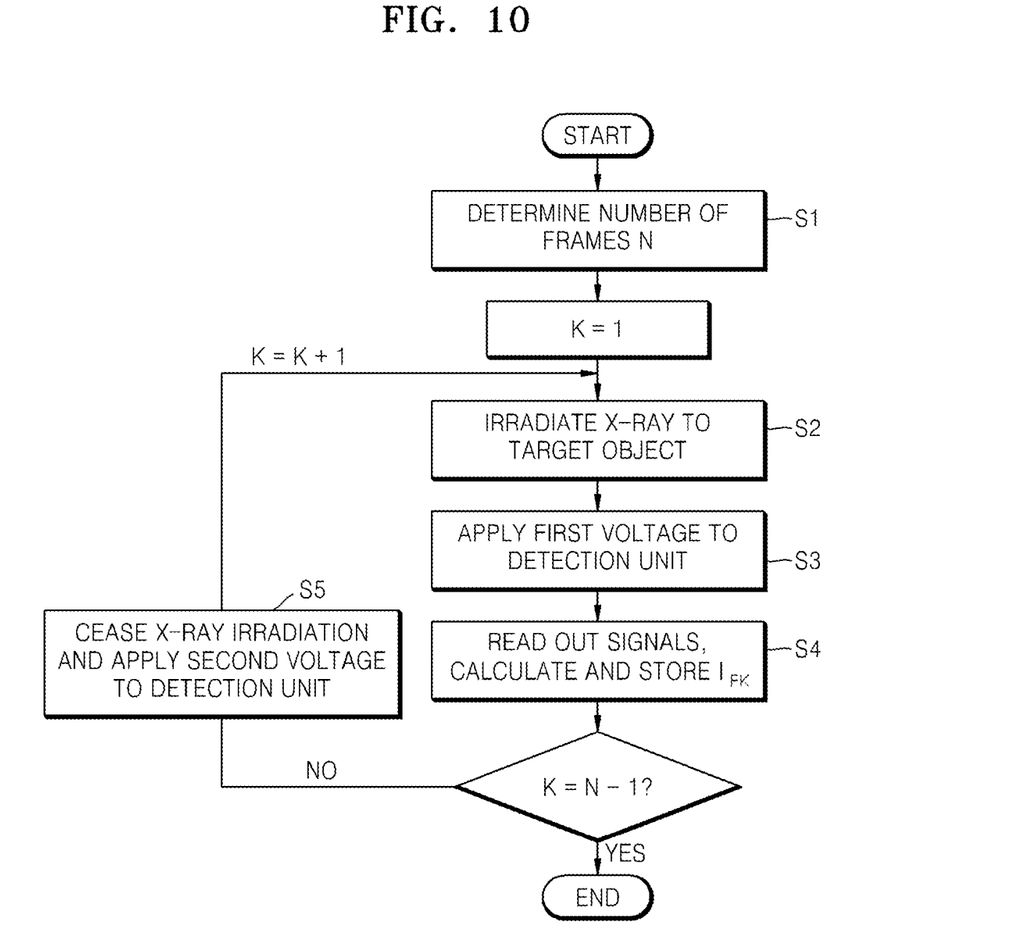
FIG. 10 is a flowchart showing an X-ray imaging method according to an example embodiment.

FIG. 10 is a flowchart showing an X-ray imaging method according to example embodiments.

Referring to FIG. 10, in operation 51 of an x-ray imaging method, the control unit 290 may determine a number of image frames N. In operation S2, the control unit 290 may instruct the X-ray emitter 100 to irradiate a target object with X-rays. Thereafter, to detect the X-rays transmitted through the target object, when the target object is exposed to X-rays in operation S2, in operation S3, the control unit 290 may instruct the bias voltage source 280 to generate a first voltage and apply the first voltage to a detection unit. The detection unit 200 may collect charges generated in response to an electrostatic field generated by the first voltage. In operation S4, after the charges are collected, the read-out circuit unit 295 may read out electric signals from the collected charges and compute data corresponding to a first frame image $I_{F1}$ from the electric signals.

Before proceeding to a next frame, in operation S5, the control unit 290 may instruct the X-ray emitter 100 to cease the X-ray irradiation. Further, the control unit 290 may instruct the bias voltage source 280 to generate the second voltage and apply the second voltage to the detection unit 200 to remove residual charges therein.

The control unit 290 may determine a magnitude of the second voltage based on a reference voltage. For example, prior to applying second voltage, the control unit 290 may perform a residual charge evaluation operation to determine an amount of residual charges remaining in a previous frame and use the amount residual charges from the previous frame as a reference for determining the second voltage V2. Alternatively, the control unit 290 may use a reference voltage associated with a previous frame to calculate the second voltage for the current frame.

After the residual charges are removed, an X-ray is irradiated to the target object for forming a next frame image, a counter K is advanced and the operations S3, S4, and S5 may be repeated for each frame except a last frame N−1 where removal of residual charges may be unnecessary. Thus, the detector may toggle between the first voltage and the second voltage by changing a voltage from the first voltage to the second voltage and then returning to the first voltage.

Accordingly, a plurality of X-ray images without an afterimage due to residual charges from previous frames may be obtained.

As described above, according to the one or more of the above example embodiments, residual charges remaining in the photoconductor layer may be removed by changing a bias voltage applied to an X-ray detection device. Therefore, according to the X-ray imaging apparatus method and an apparatus therefore, image lag due to residual charges from a previous frame image may be avoided without using a high voltage generator to apply a bias voltage of several kilovolts. As a result, high quality images may be obtained, a plurality of frames of images may be rapidly formed, and a size of a detector may be decreased due to the absence of a high voltage generator.

It should be understood that the example embodiments described herein should be considered in a descriptive sense only and not for purposes of limitation. Descriptions of features or aspects within each embodiment should typically be considered as available for other similar features or aspects in other embodiments.

What is claimed is:

1. A method of removing residual charges from a photoconductive material, the method comprising:
   applying a first voltage between two electrodes to form an electrostatic field during a collection operation in which x-rays are irradiated onto the photoconductive material, wherein a first electrode directly contacts a first end of the photoconductive material and a second electrode directly contacts a second end of the photoconductive material, the second end being opposite to the first end; and
   applying a second voltage between the two electrodes to reduce an amount of a residual charge in the photoconductive material during a removal operation,
   wherein applying the second voltage includes applying the second voltage with a polarity that is opposite to a polarity of the first voltage and an absolute value of a magnitude of the second voltage smaller than a magnitude of the first voltage.

2. The method of claim 1, wherein the first voltage has a magnitude of less than 300 volts (V) and the photoconductive material is a material configured to operate at the first voltage.

3. The method of claim 1, wherein the photoconductive material includes Mercury Iodide $HgI_2$.

4. The method of claim 1, wherein applying the second voltage to the photoconductive material to reduce the amount of the residual charge comprises applying the second voltage to the photoconductive material in a form of a plurality of pulses.

5. The method of claim 1, further comprising:
   applying visible light to the photoconductive material during the removal operation.

6. The method of claim 5, wherein applying visible light to the photoconductive material includes applying the visible light to the photoconductive material while the second voltage is applied.

7. The method of claim 1, further comprising:
   storing at least a portion of charges generated in the photoconductive material during the collection operation; and
   reading the stored charges to form a first frame image prior to the removal operation.

8. A method of forming an x-ray image, the method comprising:
   irradiating a target object with x-rays during a collection operation, at least a portion of the irradiated x-rays being transmitted through the target object onto a photoconductive material;
   applying a first voltage between two electrodes to form an electrostatic field during the collection operation, wherein a first electrode directly contacts a first end of the photoconductive material and a second electrode directly contacts a second end of the photoconductive material, the second end being opposite to the first end; and
   applying a second voltage between the two electrodes to reduce an amount of a residual charge in the photoconductive material therein during a removal operation, wherein applying the second voltage includes applying the second voltage with a polarity that is opposite to a polarity of the first voltage and an absolute value of a magnitude of the second voltage smaller than a magnitude of the first voltage.

9. The method of claim 8, wherein the photoconductive material includes Mercury Iodide $HgI_2$ and a magnitude of the first voltage is less than 300 volts (V).

10. The method of claim 8, further comprising:
    storing at least a portion of charges generated in the photoconductive material during the collection operation; and
    reading the stored charges to form a first frame image before the removal operation.

11. The method of claim 10, wherein the residual charge is removed such that residual charges from the first frame image are not present in the photoconductive material during the forming of a second x-ray image such that the second x-ray image can be formed after the removal operation without effects of the residual charges from the first frame image and without an afterimage or an image distortion.

12. An x-ray detector comprising:
    a photoconductor having a first surface and a second surface facing each other;
    a common electrode directly contacting the first surface of the photoconductor;
    at least one pixel electrode directly contacting the second surface of the photoconductor; and
    a control unit configured to:
      apply a first voltage to the photoconductor to form an electrostatic field during a collection operation in which x-rays are irradiated onto the photoconductor,
      determine, as a function of a residual charge resulting from the collection operation, at least one of magnitude or polarity of a second voltage for reducing an amount of the residual charge, the second voltage being different from the first voltage, and
      apply the second voltage to the photoconductor to reduce an amount of residual charge therein during a removal operation, the second voltage being different from the first voltage, wherein the control unit applies the second voltage with a polarity that is opposite to a polarity of the first voltage and an absolute value of a magnitude of the second voltage smaller than a magnitude of the first voltage.

13. The x-ray detector of claim 12, wherein the first voltage has a magnitude of less than 300 volts (V) and the photoconductor is configured to operate at the first voltage.

14. The x-ray detector of claim 12, wherein the photoconductor includes Mercury Iodide $HgI_2$.

15. The x-ray detector of claim 12, further comprising:
    a bias voltage source connected between the common electrode and the at least one pixel electrode, the bias voltage source configured to generate the first voltage and the second voltage based on a control signal from the control unit.

16. The x-ray detector of claim 15, further comprising:
    a charging capacitor configured to store charges received from the pixel electrodes; and
    a switch configured to provide the stored charges to a read-out circuit based on a gate voltage applied to the switch.

17. The x-ray detector of claim 15, wherein the control unit is configured to instruct the bias voltage source to generate the second voltage such that the second voltage is applied to the photoconductor as a plurality of pulses.

18. The x-ray detector of claim 15, wherein the control unit is configured to apply visible light to the photoconductor during the removal operation.

\* \* \* \* \*